United States Patent [19]
Miller et al.

[11] Patent Number: 5,122,377
[45] Date of Patent: Jun. 16, 1992

[54] ORAL DELIVERY SYSTEM FOR VETERINARY DRUGS

[75] Inventors: Larry C. Miller, Richmond, Va.; Thomas S. Ingallinera, Greenville, N.C.; Kyong K. Saw, Hammonton, N.J.

[73] Assignee: A.H. Robins, Company, Incorporated, Richmond, Va.

[21] Appl. No.: 615,417

[22] Filed: Nov. 19, 1990

[51] Int. Cl.$^5$ .................. A61K 47/00; A01N 59/00
[52] U.S. Cl. .................. 424/439; 424/724; 514/197; 514/770
[58] Field of Search .............. 424/442, 439, 724; 514/562, 197, 198, 770

[56] References Cited

U.S. PATENT DOCUMENTS

| | | | |
|---|---|---|---|
| 3,696,189 | 10/1972 | Synder | 424/442 |
| 3,996,355 | 12/1976 | Lin et al. | 514/562 |
| 4,988,679 | 1/1991 | Chaukin et al. | 514/197 |

FOREIGN PATENT DOCUMENTS

| | | |
|---|---|---|
| 6016943 | 1/1985 | Japan. |
| 1089523 | 11/1967 | United Kingdom. |

*Primary Examiner*—Thurman K. Page
*Assistant Examiner*—D. Colucci

[57] ABSTRACT

A veterinary drug delivery system suitable for oral administration to animals comprising a suitable medication, a nonvolatile oil, silicone dioxide, capric/caprylic triglyceride and/or capric/caprylic/stearic triglyceride. Flavorings can be added to enhance the taste, however, even without extra flavorings the drug delivery system in administrable form is palatable. At room temperature ay and physical analysis demonstrated no significant changes in active ingredient quality. Additionally, no separation of ingredients and no changes in overall physical appearance were noted.

9 Claims, No Drawings

ORAL DELIVERY SYSTEM FOR VETERINARY DRUGS

This invention relates to the oral administration of drugs to animals, and particularly to small domestic animals.

BACKGROUND OF THE INVENTION

Conventional solid dosage forms for veterinary drugs, such as tablets and capsules, can be expelled by the animal, and multiple dosing is often difficult because the animal learns to resist the dosing procedure. While some drugs can be administered in liquid form, others are unstable in an aqueous medium and cannot be provided as a conventional liquid. Accordingly, it is an object of this invention to provide a new delivery system for veterinary drugs.

The invention provides a palatable oral delivery system suitable for drugs that are unstable in an aqueous medium, and which animals will readily consume. In addition, the invention provides an easily handled and calibrated drug delivery composition that is easy to manufacture and use, and which is readily accepted by animals. The composition described and claimed herein can also be processed as a pourable liquid, but becomes a semisolid medium for ease of administration, proper texture, and uniformity of the drug or drugs to be dosed. This composition can be optionally flavored, to further improve its acceptance by animals.

Formulations comprising antibiotics in oil bases for veterinary applications are known, and include both liquid and solid compositions. For example, British Patent No. 1,089,523 relates to a veterinary composition for treating inflammation of mammary glands in dairy animals. This composition is for topical use, and comprises an antibiotic, a hydrophobic viscous or gel base (e.g., a petroleum-based mineral oil gelled with an aluminum soap, such as commercial aluminum monostearate), and at least 10 percent by weight of a solid, finely divided physiologically innocuous non-gelling water soluble compound of average particle size below 150 microns (e.g., sugar or salt).

The formulation described in the British "523 patent is not for oral use because the soap (e.g. aluminum stearate) makes the preparation substantially un-palatable. Furthermore, the mineral oil base is a distillate of petroleum, which poses a digestive problem if orally ingested.

Various triglycerides are used in cream and ointment formulations, but are not known in oral dosage forms, nor in combination with silicon dioxide and fixed oils as a pharmaceutical vehicle. Similarly, silicon dioxide colloidal N.F. (cabosil) is not known in orally administrable, paste form. Colloidal silicone dioxide is an extremely fine non-gritty powder which is known as a solid thickener or suspending agent, and has been used as a diluent in tablets.

An antibiotic in hydrophobic colloidal silicon for veterinary administration is disclosed in Japanese Patent No. 60-169431. However, the disclosed formulation is not suitable for oral administration and the reference does not disclose the possibility of incorporating colloidal silicone with triglycerides.

SUMMARY OF THE INVENTION

In its simplest form, the oral drug delivery system, according to the invention, comprises a medication to be administered, a suitable oil such as those obtained from plant or animal tissue extract, silicon dioxide, and one or more triglycerides (preferably caprylic/capric triglycerides and/or caprylic/capric/stearic triglycerides). Flavors, oils, and preservatives can be added as desired. The amount of the drug to be dosed can vary generally from 1 to 20 percent of the final composition. Silicon dioxide comprises approximately 1 to 5 percent of the final composition, while the triglycerides are present as approximately 60 to 80 percent.

It has been found that an orally ingestable, nonaqueous gel can be prepared by combining a fixed oil (a non-volatile oil) with silicon dioxide. When a therapeutic agent is added, such as an antibiotic, a stable suspension can be obtained. According to the invention, the final product, including the therapeutic agent such as a beta-lactam antibiotic, remains stable for at least two years, without refrigeration for storage temperatures up to 45 degrees celsius.

The use of a triglyceride, such as capric/caprylic triglyceride, results in an orally palatable and stable pharmaceutical vehicle. The further use of a capric/caprylic/stearic triglyceride has been found to facilitate processing and improve stability and texture by forming a semisolid composition at room temperature which liquefies when heated. Thus, processing and pourability at slightly elevated temperatures (e.g., 40° to 50° C.) can be improved.

Capric/caprylic and capric/caprylic/stearic triglycerides are fatty acid esters of glycerol.

These triglycerides have the generic formula:

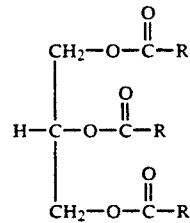

Where R is the hydrocarbon chain portion of either capric, caprylic or stearic acids attached to the carboxylic acid group, —COOH.

One suitable capric/caprylic triglyceride is Miglyol ® 812, which is available from HULS Chemicals, formerly Dynamit Nobel Chemicals. Miglyol ® 812 is a neutral oil comprising a mixed acid triglyceride of fractionated $C_8$–$C_{10}$ coconut fatty acids. Miglyol ® 812 is known for a wide variety of pharmaceutical and cosmetic applications, including oral administration of liquid dosage forms. However, it has not heretofore been known in a veterinary paste, and in surprising contrast to the composition of the invention, remains liquid at 0° C.

A suitable capric/caprylic/stearic triglyceride is Softisan ® 378, which is available from Huls America, Inc. Softisan ® 378 is a viscous triglyceride mixture derived from selected saturated $C_8$–$C_{10}$ coconut oil fatty acids. It is known for external pharmaceutical and cosmetic applications, but heretofore has not been used for oral veterinary administration of drugs, nor in combination with oils, other triglycerides, and flavorings to provide a palatable veterinary paste.

The dosage form of the invention is palatable, can be flavored, and can be administered as a paste which can be ejected into the mouth of an animal through a tube or syringe with a tapered orifice. The syringe can be metered to provide accurate dosing. For example, a 15 ml syringe can be marked to dispense accurate doses over a 5 to 10 day course of treatment.

Because of its "sticky" consistency, the paste can not easily drip out or be expelled once it is in the mouth. It is substantially free of air bubbles and voids, which minimizes inaccurate dosing. Ideally, the viscosity and texture of the paste are such that it will readily exit the syringe and break free cleanly when dispensed. No paste should be lost, as by oozing from the syringe. In addition, the composition has a shelf life of at least two years and does not require refrigeration, will stay in suspension without shaking, does not separate even in extended storage in temperatures up to 45° C., and does not contain sugar.

In a preferred embodiment, the viscosity of the formulation can be modified by heating and cooling. This improves manufacturing and handling characteristics, by providing a less viscous pourable composition when warmed gently (e.g., 40° to 50° C.). At room temperature, the composition is more viscous, and forms a paste suitable for administration to animals. This variable viscosity can be achieved by adjusting the amount of capric/caprylic and capric/caprylic/stearic triglycerides in the composition, as by adding Softisan 378 as a congealing agent.

DETAILED DESCRIPTION

A typical composition, according to the invention, contains approximately 3 to 6 percent flavors and oils, 1 to 5 percent silicon dioxide, 60 to 80 percent capric/caprylic triglyceride, and 1 to 20 percent therapeutic agent. Alternatively, 20 to 50 percent capric/caprylic/stearic triglyceride can be used, together with 40 to 50 percent capric/caprylic triglyceride.

Formulations that are typical of the invention are set forth in the following examples. It will be understood that these examples are illustrative, and do not serve to limit the scope of the invention or the appended claims.

EXAMPLE 1 — Amoxicillin Gel

A stable suspension of Amoxicillin in a pharmaceutically acceptable gel was prepared from the following ingredients:

| Ingredient | Batch A |
| --- | --- |
| peanut oil | 72 g |
| cod liver oil | 10 g |
| Cabosil (SiO$_2$) | 8 g |
| Amoxicillin | 10 g |
| | 100 g |

Cabosil is silicon dioxide colloidal N.F. Amoxicillin is a known antibiotic that is related to ampicillin and is suitable for oral use. It has a broad range of indications, including efficacy against meningococcus, pneumococcus, and gonococcus bacteria. It is often provided as Amoxicillin trihydrate, which is a solid.

Batch A was made by weighing the oils into a beaker, adding the Cabosil, and stirring until a thick gel was formed. The Amoxicillin was obtained from 500 mg capsules, the contents of which were ground into a fine powder with a mortar and pestle. (The capsules themselves were discarded). The gel and Amoxicillin were combined and mixed well, to form a stable suspension of the Amoxicillin in the gel base.

It should be noted that the order in which these materials are combined is not critical. Thus, a second suspension was made from the same ingredients, by adding the Amoxicillin to the oil, stirring well, and thereafter adding Cabosil to the solution and blending to form a gel. The Amoxicillin gel remained stable at room temperature, and did not separate.

EXAMPLE 2 — Palatable Triglyceride—Amoxicillin Paste

Two stable suspensions of Amoxicillin in a palatable and pharmaceutically acceptable paste were prepared from the following ingredients:

| Ingredient | Batch B | Batch C |
| --- | --- | --- |
| Miglyol | 35.5 g | 35.5 g |
| cod liver oil | 5.0 g | 5.0 g |
| Cabosil (SiO$_2$) | 4.0 g | 4.0 g |
| Amoxicillin | 5.0 g | 5.0 g |
| Tween 60 | 0.5 g | — |
| Span 60 | — | 0.5 g |

Miglyol is a capric/caprylic triglyceride, as described above. Tween ® 60 and Span ® 60 are surfactants which are suitable for veterinary ingestion, and are available from ICI United States, Inc.

For each batch, the oil, triglyceride (Miglyol), and surfactant (Tween 60 or Span 60) were combined in a beaker, and then Amoxicillin was added. Cabosil (SiO$_2$) was added thereafter with mixing to form a gel, which gel was run through a roller mill to produce a paste having a smooth and uniform consistency. A colloidal mill can also be used.

Similarly, another 5 batches were prepared, without Amoxicillin, using the following ingredients:

| Ingredient | Batch D | Batch E | Batch F | Batch G | Batch H |
| --- | --- | --- | --- | --- | --- |
| Miglyol | 35.5 g | 35.5 g | 35.5 g | 35.5 g | 35.5 g |
| cod liver oil | 5.0 g | 5.0 g | 5.0 g | 5.0 g | 2.5 g |
| Cabosil (SiO$_2$) | 2.0 g | 3.0 g | 2.5 g | 2.5 g | 2.0 g |
| Surfactant: | | | | | |
| Tween 20 SD | 0.5 g | — | — | — | — |
| Span 60 | — | 0.5 g | — | — | — |
| Brij 93 | — | — | 0.5 g | — | — |
| Imwitor 780K | — | — | — | 0.5 g | 0.3 g |

Brij ® 93 and Imwitor ® 780K are surfactants suitable for veterinary ingestion and are available from ICI United States, Inc. and HULS Chemicals, respectively. For each batch, the oil, triglyceride (Miglyol), and surfactant were combined, and then the Cabosil was added, with mixing, to form a gel. Each batch resulted in a suitable pharmaceutical vehicle, and it was found that the texture and viscosity could be modified as desired by varying the amount of Cabosil, and/or by using different surfactants. In this Example, the preferred embodiments were Batches D and H. However, it will be appreciated that the formulation can be readily modified by practitioners to satisfy a wide range of needs and applications.

EXAMPLE 3 —Palatable Triglyceride—Amoxicillin Paste

Two stable suspensions of Amoxicillin in a palatable and pharmaceutically acceptable gel were prepared from the following ingredients, in amounts per 1800 g:

| Ingredient | Batch I | Batch J |
| --- | --- | --- |
| capric/caprylic triglyceride (Miglyol 812) | 1521.0 g | 1417.5 g |
| cod liver oil USP | 63.0 g | 63.0 g |
| Cabosil (colloidal $SiO_2$, N.F.) | 81.0 g | 72.0 g |
| Amoxicillin trihydrate USP | 112.5 g | 225.0 g |
| Tween 20 SD (Polysorbate, N.F.) | 18.0 g | 18.0 g |
| saccharin sodium | 0.9 g | 0.9 g |
| sausage flavor (Hercules ® 1459) | 3.6 g | 3.6 g |

The pharmaceutical paste, according to the invention, was prepared by weighing the cod liver oil, surfactant (Tween 20), and triglyceride (Miglyol) into a suitable container, mixing, and adding saccharin sodium (a sweetener), sausage flavor (e.g., a proprietary formulation of Hercules, Inc.), and amoxicillin trihydrate, also under mixing. Miglyol 812 was slowly added to this mixture, under slow mixing with a suitable stirrer, to form a thick paste.

This paste was then run through a triple roller mill adjusted to 0.004 inches (0.10 mm) and/or 0.002 inches (0.05 mm), respectively, to provide a smooth homogeneous paste. A colloidal mill can also be used. The paste was then loaded into 15 ml calibrated dosage syringes in 12.5 g measures, with occasional compacting to remove any trapped air. Each syringe was supplied with a Santoprene plunger seal and cap, and with a tip cap.

The resulting product was a thick, off-white paste with a sausage flavor, containing 62.5 mg/g (Batch I) and 125 mg/g (Batch J) of Amoxicillin trihydrate.

EXAMPLE 4 —Palatable & Liquefiable Amoxicillin Paste

This example shows an embodiment of the invention wherein the Amoxicillin paste is a palatable semisolid at room temperature, but can be liquefied when warmed, for example to between 40° and 50° C. These formulations are easier to prepare, and result in improved texture and stability.

Three formulations were prepared as follows:

| Ingredient | Batch K | Batch L | Batch M |
| --- | --- | --- | --- |
| Miglyol 812 | 600.0 g | 30.0 g | — |
| Softisan 378 | 268.5 g | 20.0 g | 40.0 g |
| cod liver oil | 35.0 g | — | — |
| Cabosil ($SiO_2$) | 21.5 g | 21.5 g | — |
| Amoxicillin | 62.5 g | 2.67 g | 2.67 g |
| Tween 20 SP | 10.0 g | — | — |
| saccharine sodium | 0.05 g | — | — |
| sausage flavor | 2.0 g | — | — |

Softisan 378 is a capric/caprylic/stearic triglyceride, as described above. Batch K was prepared by weighing out the cod liver oil, Tween 20, saccharine sodium, Softisan 378 and Miglyol 812 into a suitable container. These ingredients were warmed to between 40° and 45° C. while mixing. The Softisan melted, and an opaque solution was obtained. (As shown below, the viscosity of this solution was measured at 40° C. and at room temperature.)

Colloidal silicon dioxide (Cabosil) was added to the warm solution, and a smooth and uniform solution was obtained. (The viscosity again was measured at 40° C. and at room temperature.) This solution was passed through a roller mill (with settings of 0.004 and 0.002 inches), and the viscosity was measured again.

Although this batch (Batch K) appeared pourable, in fact it was not, and at 50° C. its viscosity was the same as at room temperature.

Batch L was prepared in substantially the same way, with a change in the proportion of ingredients. The Softisan 378 and Miglyol 812 were measured into a beaker, mixed well, and warmed to between 40° and 45° C. until melted. Amoxicillin was mixed in, and the resulting formulation was passed through a roller mill as before. Then, Cabosil was added and the mixture was stirred until smooth and creamy. At room temperature, the viscosity of this formulation was that of a thick paste, but at 35° to 40° C. the viscosity decreased, and a thick but pourable paste resulted. At 45° to 50° C., the viscosity increased again, and the paste thickened to the same consistency it had at room temperature.

Batch M was a mixture of Amoxicillin and Softisan 378. This mixture became solid and unusable at room temperature.

From these experiments it was determined that an easy to handle pourable mixture can be maintained at temperatures of 40°–50° C., and these same formulations solidify into a palatable and readily administered paste when cooled to room temperature.

EXAMPLE 5 —A preferred Embodiment of the Invention

In a preferred embodiment of the invention, a 20 kg batch was prepared as shown below. The product is an off-white, sausage-flavored thick paste containing 67.17 mg/g (Batch N) and 134.34 mg/g (Batch O) of amoxicillin trihydrate, and is dosed in a 15 ml calibrated syringe. A preferred dose, per administration, is 55 mg/dose for formulation Batch N, and 110 mg/dose for Batch O.

| Ingredient | Batch N (g) | Amoung/g (mg) |
| --- | --- | --- |
| capric/caprylic triglyceride (Miglyol 812) | 9257 | 462.83 |
| capric/caprylic/stearic triglyceride (Softisan 378) | 8000 | 400.00 |
| cod liver oil USP | 700.00 | 35.00 |
| Cabosil (colloidal $SiO_2$, N.F.) | 320.00 | 16.00 |
| Amoxicillin trihydrate USP | 1343.00 | 67.17 |
| Tween 20 SD (Polysorbate, N.F.) | 200.00 | 10.00 |
| saccharin sodium | 10.0 | 0.50 |
| sausage flavor (N&A OS-520189U) | 120.00 | 6.00 |
| tBHQ Antioxidant | 50.0 | 2.50 |

| Ingredient | Batch O (g) | Amoung/g (mg) |
| --- | --- | --- |
| capric/caprylic triglyceride (Miglyol 812) | 8433.2 | 421.66 |
| capric/caprylic/stearic triglyceride (Softisan 378) | 7500 | 375.00 |
| cod liver oil USP | 700.00 | 35.00 |
| Cabosil (colloidal $SiO_2$, N.F.) | 320.00 | 16.00 |
| Amoxicillin trihydrate USP | 2686.80 | 134.34 |
| Tween 20 SD (Polysorbate, N.F.) | 200.00 | 10.00 |

-continued

| Ingredient | Batch O (g) | Amoung/g (mg) |
| --- | --- | --- |
| saccharin sodium | 10.0 | 0.50 |
| sausage flavor (N&A OS-520189U) | 120.00 | 6.00 |
| tBHQ Antioxidant | 50.0 | 2.50 |

These batches were made by screening amoxicillin trihydrate USP through a No. 60 mesh screen. The Softisan was weighed into a suitable container, such as a 24 liter stainless steel vessel, as was warmed to 40°-45° C. by using a hot water bath, until the Softisan melted. The tBHQ was then added and dissolved. In a separate container, such as a 36 liter stainless steel vessel, the Miglyol, Tween, cod liver oil, saccharine sodium and sausage flavor were weighed and mixed well. Then, while maintaining the temperature at 40°-45° C., the melted Softisan/tBHQ mixture was added and mixed well. The amoxicillin and cabosil were then added, with mixing using a propeller-type mixer.

The resulting mixture was passed through a colloidal mill with a No. 3 opening and a rheostat setting of 60, and a thick homogeneous paste pourable at 40°-45° C. was obtained. While maintaining this temperature, syringes or other dosage containers were easily filled. When the paste cooled, it semi-hardened into a thick, palatable paste that was suitable for oral administration.

The final product can be administered orally, using a dosage syringe, or by inducing the animal to lick a dispensed quantity from a surface, such as the animal's paw.

Twenty six week studies show excellent storage stability for both formulations, Batch N and Batch O. These studies were conducted at 4, 25 and 37 degrees centigrade, simulating cold, room temperature and warm storage, respectively. Both analytic assay and physical analysis demonstrated no significant changes in active ingredient quality. Additionally, no separation of ingredients and no changes in overall physical appearance were noted.

What is claimed is:

1. A composition for oral delivery of veterinary medication comprising:
   a therapeutic agent selected from the group consisting of amoxicillin, ampicillin and the trihydrate salt thereof;
   a non-volatile oil;
   silicon dioxide; and
   capric/caprylic triglyceride.

2. The composition of claim 1 further comprising a surfactant suitable for veterinary ingestion.

3. The composition of claim 1 wherein said therapeutic agent is between 1 to 20 percent by weight, said silicon dioxide is between 1 to 5 percent by weight, and said triglyceride is between 60 to 80 percent by weight of total composition.

4. The composition of claim 1, further comprising a capric/caprylic/stearic triglyceride.

5. The composition of claim 4, wherein said therapeutic agent is between 1 to 20 percent by weight, said silicone dioxide is between 1 to 5 percent by weight said capric/caprylic/triglyceride is between 40 to 50 percent by weight, and said capric/caprylic/stearic triglyceride is between 20 to 50 percent by weight of total composition.

6. A stable, extended shelf-life, palatable oral delivery system for administering veterinary drugs comprising:
   a beta-lactam therapeutic agent;
   a non-volatile oil extracted from plant or animal tissue;
   silicon dioxide;
   capric/caprylic triglyceride;
   a surfactant suitable for veterinary ingestion; and
   flavor enhancing additives.

7. The oral delivery system of claim 6, wherein said therapeutic agent is between 1 to 20 percent by weight, said silicon dioxide is between 1 to 5 percent by weight, and said triglyceride is between 60 to 80 percent by weight of total composition.

8. The composition of claim 4, wherein said composition is a palatable, semi-solid paste suitable for oral administration at room temperature, and is a pourable liquid at temperatures between 40 to 50 degrees celsius.

9. The composition of claim 8 wherein said therapeutic agent is between 1 to 20 percent by weight, said silicon dioxide is between 1 to 5 percent by weight, said capric/caprylic triglyceride is between 40 to 50 percent by weight, and said capric/caprylic/stearic triglyceride is between 20 to 50 percent by weight of total composition.

* * * * *